(12) United States Patent
Bertling et al.

(10) Patent No.: US 6,261,809 B1
(45) Date of Patent: Jul. 17, 2001

(54) METHOD FOR MARKING SOLID, LIQUID OR GASEOUS SUBSTANCES

(75) Inventors: Wolf Bertling, Erlangen; Hans Kosak, Bonn, both of (DE)

(73) Assignee: november Aktiengesellschaft Gesellschaft fur Molekulare Medizin, Erlangen (DE)

( * ) Notice: Subject to any disclaimer, the term of this patent is extended or adjusted under 35 U.S.C. 154(b) by 0 days.

(21) Appl. No.: 09/486,884

(22) PCT Filed: Sep. 4, 1998

(86) PCT No.: PCT/DE98/02615

§ 371 Date: Mar. 3, 2000

§ 102(e) Date: Mar. 3, 2000

(87) PCT Pub. No.: WO99/13102

PCT Pub. Date: Mar. 18, 1999

(30) Foreign Application Priority Data

Sep. 5, 1997 (DE) .............................. 197 38 816

(51) Int. Cl.$^7$ ...................................... C12P 19/34
(52) U.S. Cl. .................. 435/91.2; 435/5; 435/6; 435/91.1; 435/91.2; 427/7; 427/145; 427/337; 427/338; 283/73; 283/74; 283/95; 283/98; 283/100; 118/31.5; 118/201
(58) Field of Search ................. 435/5, 6, 91.1, 435/91.2; 427/7, 145, 338, 337; 118/31.5, 201; 283/73, 74, 95, 98, 100

(56) References Cited

FOREIGN PATENT DOCUMENTS

WO 97/32040 * 9/1997 (WO) ........................ 435/6

\* cited by examiner

Primary Examiner—W. Gary Jones
Assistant Examiner—Janell E. Taylor
(74) Attorney, Agent, or Firm—Fish & Richardson P.C., P.A.

(57) ABSTRACT

The invention relates to a method for marking solid, liquid or gaseous substances, whereby the substance to be marked is provided with at least one synthetically produced nucleic acid sequence. Said nucleic acid sequence contains a first sequence section constructed with the 5' terminal end, a second sequence comprised of at least two bases and connected to said nucleic acid sequence, and a third sequence section constructed with the 3' terminal end and connected to the said nucleic acid sequence. In order to simplify the identification of the marking, the invention provides that a first primer group is used with a first primer section corresponding to the first sequence section and a second primer group is used with a third primer section corresponding to the third sequence section. Every primer group four comprises differing primer variants in at least one additional respective base which is provided on the end so that exactly one primer variant of the first primer group together with exactly one primer variant of the second primer group is complimentary to the nucleic acid sequence.

32 Claims, 7 Drawing Sheets

FIG. 1

| | BASE 20 | BASE 21 |
|---|---|---|
| 1 | A | A |
| 2 | A | T |
| 3 | A | G |
| 4 | A | C |
| 5 | T | A |
| 6 | T | T |
| 7 | T | G |
| 8 | T | C |
| 9 | G | A |
| 10 | G | T |
| 11 | G | G |
| 12 | G | C |
| 13 | C | A |
| 14 | C | T |
| 15 | C | G |
| 16 | C | C |

1. PCR CYCLE

2. BIS N-TER PCR CYCLE

1. LCR CYCLE

2. BIS N-TER CYCLE LCR CYCLE

LIGATION OF THE
PRIMER DNA

METHOD FOR MARKING SOLID, LIQUID OR GASEOUS SUBSTANCES

The invention relates to a process according to the precharacterizing clause of marking a solid, liquid, or gaseous substance. It furthermore relates to a kit for carrying out the process.

Such a process is disclosed in U.S. Pat. No. 5,643,728. In this process, the marking is contained in a specific sequence section of a nucleic acid sequence. For identification of the marking, the nucleic acid sequence is duplicated using the polymerase chain reaction (PCR). The marking containing [sic] in the duplicated product is then identified by means of sequencing.

A further process is disclosed in DE 44 39 896 A1. In this process, the DNA molecules added to the substance to be marked accommodate a linear polymorphism which carries the marking. For identification of the marking, the DNA molecules are duplicated by means of PCR and then subjected to gel electrophoresis. The band sequence which can be observed as a result of the gel electrophoresis represents the marking, similarly to a bar code. The band sequence can also be translated into a number.

The previously mentioned processes are disadvantageous in a number of respects:

a) The processes are time- and cost-consuming, because for the identification of the marking, a PCR and a gel electrophoresis have to be carried out;
b) the processes are difficult to automate, because the reaction products formed in the PCR have to be transferred to a gel for carrying out the gel electrophoresis;
c) the processes are error-prone, because a large number of contamination-sensitive pipetting operations are necessary to carry them out;
d) the processes are laborious because, for marking a large number of substances, the same number of labeling DNAs have to be prepared.

A further process is disclosed in U.S. Pat. No. 5,139,812. Here, an ink containing [lacuna] specified nucleic acid sequence is used for the falsification-proof marking of articles. In order to mark a plurality of articles in a distinguishable manner, different inscriptions are applied using the ink. For the identification of a marking applied in such a way, the inscription is rendered visible by means of a color reaction. Identification can also be carried out by a radioactive marking of the nucleic acid sequence used. This process is therefore especially disadvantageous, because the application of a distinguishable marking is troublesome and the marked article has to be destroyed for identification.

It is furthermore disclosed in WO 95/17737 to use the artist's blood for marking works of art. For identification, the marking is compared by means of DNA analysis with a deposited further blood sample. This process does not make possible the preparation of a large number of different markings without problems. Identification is laborious.

The object of the invention is to indicate a process and a kit for carrying it out with which a large number of substances or articles can be marked in a falsification-proof and distinguishable manner and can subsequently be identified in an inexpensively and rapidly. This object is achieved by the features of claims 1 and 20. Expedient embodiments of the invention result from the features of claims 2 to 19 and 21 to 27.

According to the achievement of the invention as regards the process, it is proposed that, for identification, a first primer group having a first primer section corresponding to the first sequence section and a second primer group having a third primer section corresponding to the third sequence section is used, where each of the primer groups comprises four primer variants, in each case differing in at least one additional terminally provided base, such that just one primer variant of the first primer group together with just one primer variant of the second primer group makes possible amplification of the nucleic acid sequence.

Using the process according to the invention, a distinguishable marking or internal numbering of a large number of articles can be carried out simply. Using a relatively small number of different marking or nucleic acid sequences, a large number of different markings can be made available. The markings are identifiable rapidly and without great expenditure.

According to one embodiment of the invention, the nucleic acid sequence has more than 20, preferably 40, nucleotides.

Nucleic acid sequences which differ in the second sequence section are advantageously used for marking. This advantageously consists of two part regions, of which each is occupied by at least one base. The combination of the two part regions makes possible the preparation of a total of 16 different nucleic acid variants, namely adenine (=A)–A, A-thymidine (=T), A-guanine (=G), A-cytosine (=C), T-A, T-T, T-G, T-C, G-A, G-T, G-G, G-C, C-A, C-T, C-G, C-C. The 16 nucleic acid variants form a nucleic acid set.

Advantageously, the second sequence section is formed of two part regions, of which at least one consists of a plurality of bases. Accordingly, the corresponding primer variant is then terminally provided with the same number of corresponding bases. As a result, the probability of the formation of false-positive samples is drastically reduced. The part region can consist of a specific sequence or of a number of identical bases.

To increase the combination possibilities, further nucleic acid sets can be used whose nucleic acid variants differ in the first and third sequence section. For example, to increase the combination possibilities from 16 to $16^2$, the previously described nucleic acid variants of a nucleic acid set can be combined with further nucleic acid variants which are selected from a second nucleic acid set. The second nucleic acid set differs from the first nucleic acid set in the first and third sequence section. Analogously, the coding capacity can be increased to $16^n$ by the use of n nucleic acid sets.

The first and the third sequence section preferably have the same number of nucleotides. The first and the third sequence section are expediently constructed such that they are fusible under comparable stringency conditions. This makes possible a very simple amplification by means of polymerase chain reaction (PCR) or ligase chain reaction (LCR).

The nucleic acid sequences used can, of course, also be nucleic acid derivative sequences, in particular protein-like nucleic acid (PNA) or phosphortionate [sic] nucleic acids (PTO) or hybrids thereof. Nucleic acid derivative sequences of this type are in some cases distinguished by improved stability.

To protect one or more nucleic acid sequence(s) applied to solid articles, these can be covered by a protective layer, such as wax. The nucleic acid sequence(s) can furthermore be a constituent of a layer applied to solid articles, such as a lacquer. Marking can also be brought about by impregnation or mixing.

For identification of the at least one nucleic acid sequence, this is expediently extracted and a solution containing the nucleic acid sequence is prepared. The nucleic acid sequence can then be duplicated by means of PCR or LCR using the primer variants. The duplicated nucleic acid sequence or the amplificate is expediently subsequently detected by means of fluorescence, DNA, gel electrophoresis, restriction analysis, hybridization or by means of sequencing. Detection by means of fluorescence is particularly simple and quick to carry out. It can take place directly in a microtiter plate.

According to the invention, to carry out the process, a kit for the identification of a marking [lacuna], where the kit has a first primer group having a first primer section corresponding to the first sequence section and a second primer group having a third primer section corresponding to the third sequence section, where each of the primer groups comprises four primer variants, in each case differing in at least one additional terminally provided base, such that just one primer variant of the first primer group together with just one primer variant of the second primer group is complementary to the nucleic acid sequence.

Advantageously, the primer variants have the same or a similar number of nucleotides. They can have, in particular, more than 10 nucleotides, preferably 20 nucleotides. In particular, all primer variants are fusible with the nucleic acid sequence under similar or comparable stringency conditions.

To facilitate handling, each of the primer variants can be absorbed separately by a carrier, where the carrier is/are [sic] a solution, a plastic and/or microcapsules. It is regarded as particularly advantageous that two different primer variants in each case are present as a mixture, where one primer variant is selected from the first primer group and the other primer variant is selected from the second primer group.

The kit can, of course, also contain further primer groups, of which each in each case contains a primer variant complementary to a further nucleic acid set.

The process and the kit are suitable, in particular, for the marking and identification of solid substances, such as currency, documents, data media and the like. Likewise, liquid substances, in particular medicaments, chemicals, foodstuffs and gaseous substances of that type, in particular waste gases and such like, can be marked and identified.

Below, an exemplary embodiment of the invention will be described with the aid of the drawing. In this

Figure 1:
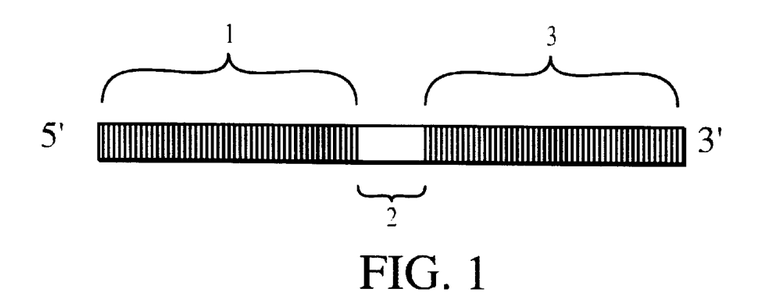
FIG. 1 shows a nucleic acid sequence represented schematically.

In FIG. 1, a nucleic acid sequence is shown schematically. It consists of a first 1 sequence section [sic] forming the 5'-terminal end, a second sequence section 2 connected therewith, which is in turn connected to a third sequence section 3 forming the 3'-terminal end.

Figure 2:
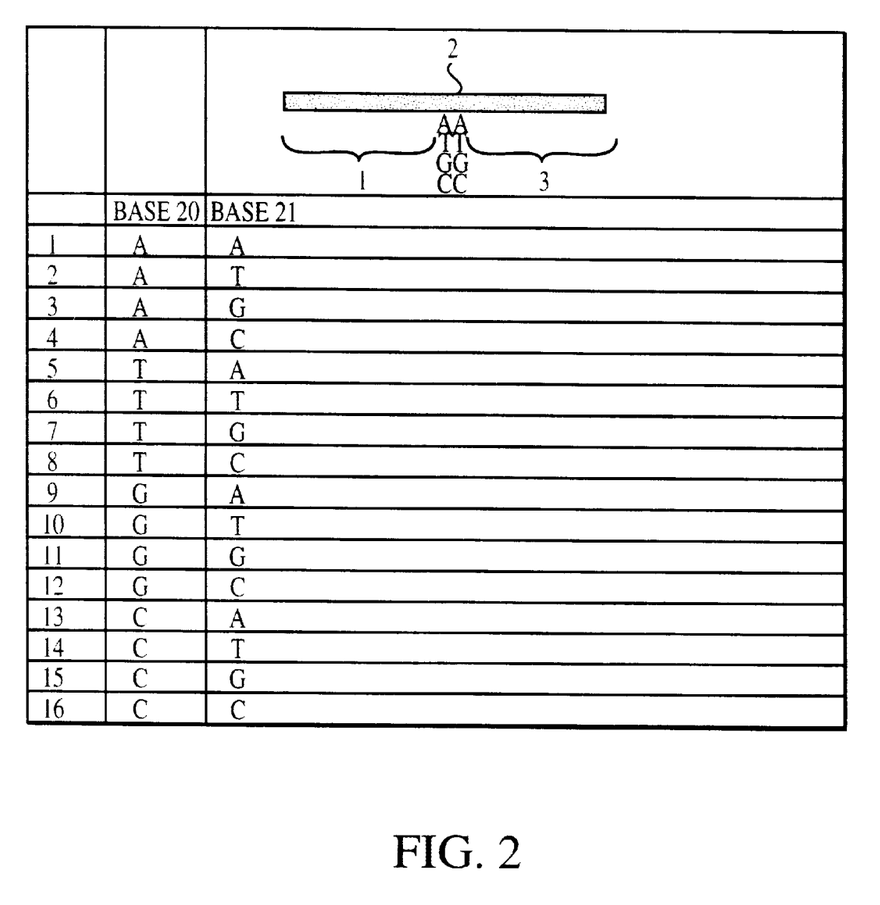
FIG. 2 shows a tabular overview of the combination possibilities of the second sequence section.

In a tabular overview, FIG. 2 schematically shows the different nucleic acid variants resulting from a variation in the bases of the second sequence section. The first sequence section 1 and the third sequence section 3 consist of nineteen bases in each case. The second sequence section 2 connecting these two sequence sections consists of two bases. A here represents the base adenine, G guanine, C cytosine and T thymidine.

The two bases of the second sequence section occupy positions 20 and 21 of the nucleic acid sequence. As can be seen FIG. 2, with a constant first and third sequence section 1 and 3 due to different occupation of the two bases of the second sequence section 2 sixteen different nucleic acid variants can be prepared. It is possible by means of the sixteen nucleic acid variants to prepare sixteen different markings.

Figure 3:
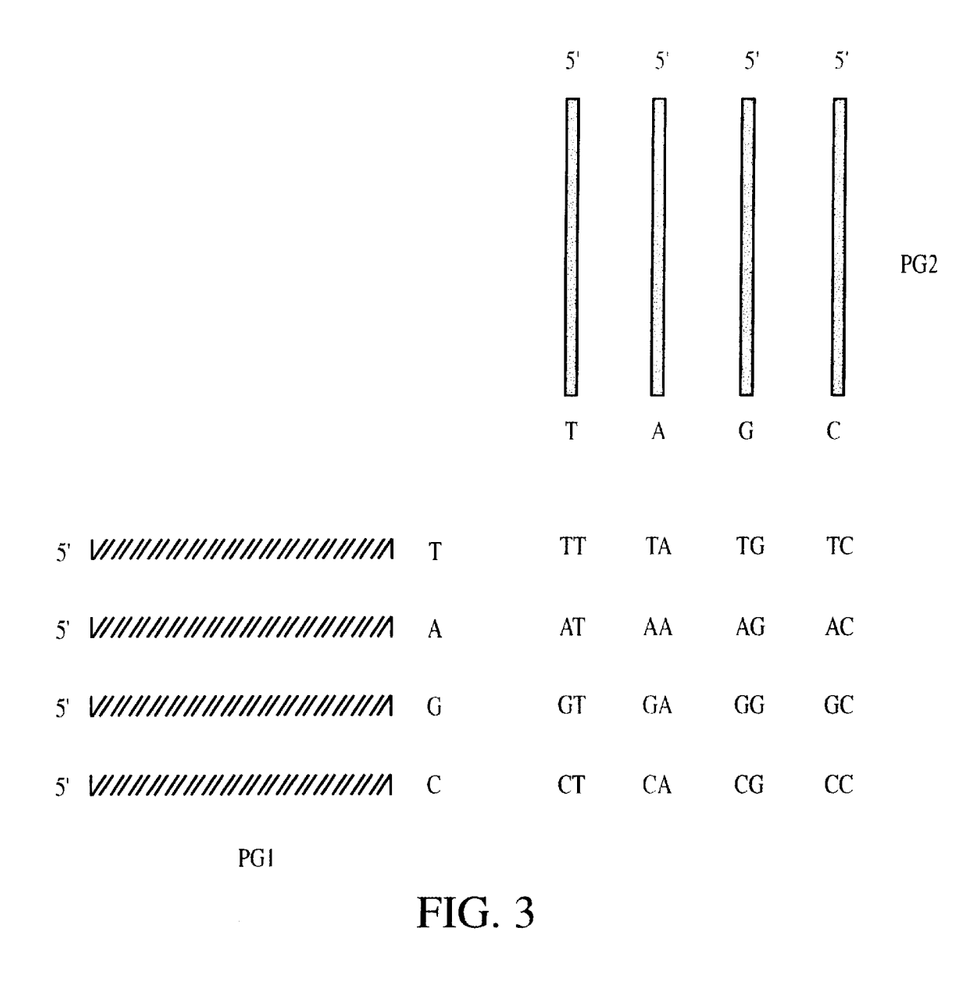
FIG. 3 shows an overview of the combination possibilities with 2×4 primer variants in the PCR.

FIG. 3 describes the combinations which are possible with a first PG1 and a second primer group PG2 each having four primer variants. The 5' section of the primer variants is complementary to the first or third section of the nucleic acid sequence N. The 3' end of the primer variants in each case carries one of the four bases A, T, G, C. By combination of the primer variants of the first PG1 and the second primer group PG2, 16 different sequences can be hybridized in the second sequence section 2 of the nucleic acid sequence N.

For identification, in particular of a nucleic acid sequence only differing in the second sequence section, this is first brought into solution. The solution is subjected to a PCR. As can be seen from FIG. 4, primers are used here which only hybridize with the first and third sequence section 1 and 3 if agreement also exists with the base of the second sequence section 2 in each case connecting thereto. For carrying out the PCR and thus for identification of the nucleic acid sequence, two groups of different primers are accordingly necessary. A first primer group PG1 has a first primer section corresponding to the first sequence section 1; a second primer group PG2 has a third primer section corresponding to the third sequence section 3. Each of the primer group [sic] PG1, PG2 comprises four primer variants PV1–PV8, which differ in the base provided terminally in each case.

Figure 4:
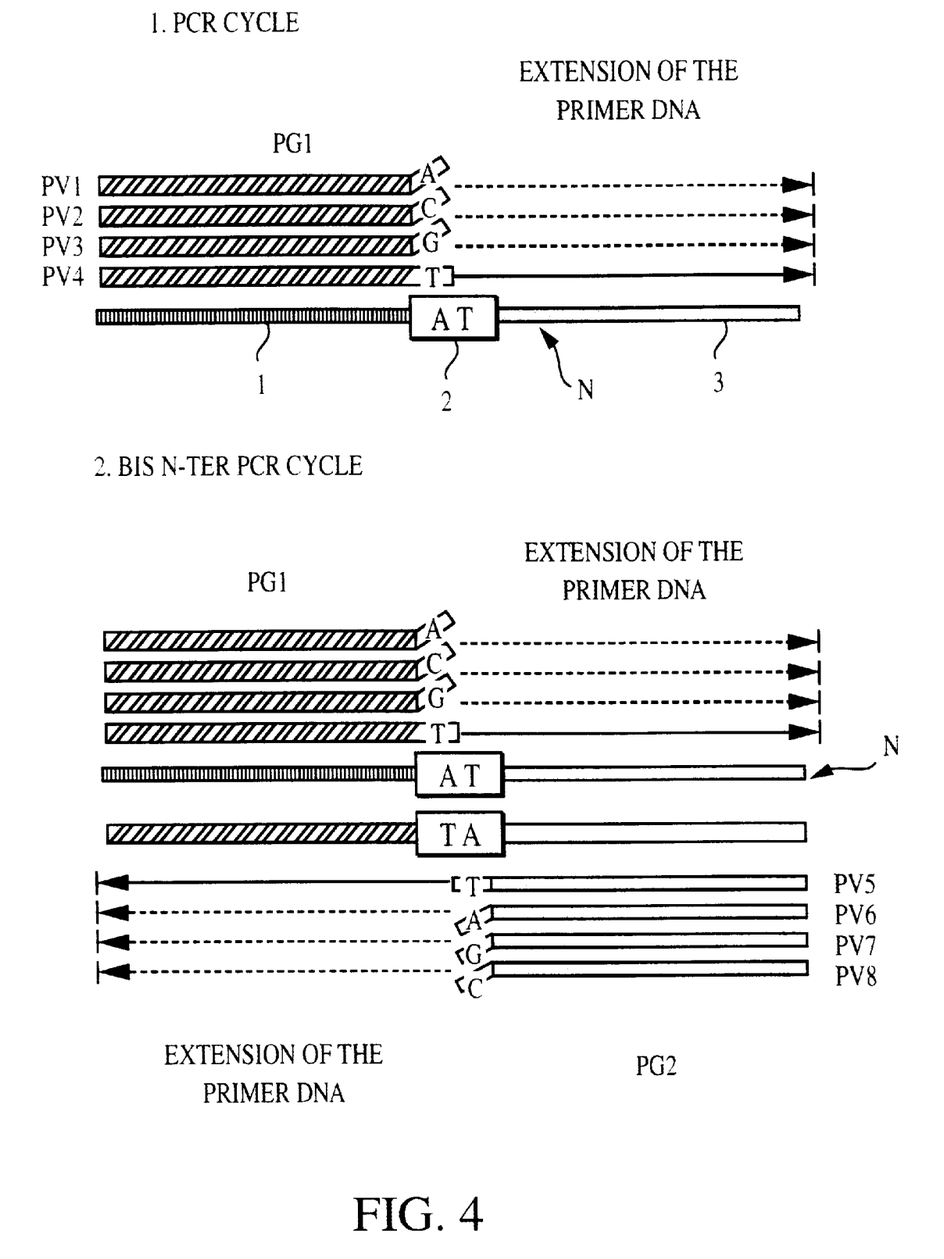
FIG. 4 shows a schematic representation of the functional mechanism of the duplication of the nucleic acid sequences by means of PCT [sic]

For identification, a primer variant PV1–PV4 of the first primer group PG1 is in each case combined with a primer variant PV5–PV8 of the second primer group PG2. Sixteen possible combinations result. The nucleic acid sequence-containing solution to be identified is subjected to a PCR of each of the sixteen combinations. Amplification is only observed where the primer combination allows hybridization with the nucleic acid sequence to be identified. Identification can take place, for example, in that the amplificate fluoresces. The identified nucleic acid sequence can be assigned a specified numerical value. This numerical value represents the code.

Figure 5:
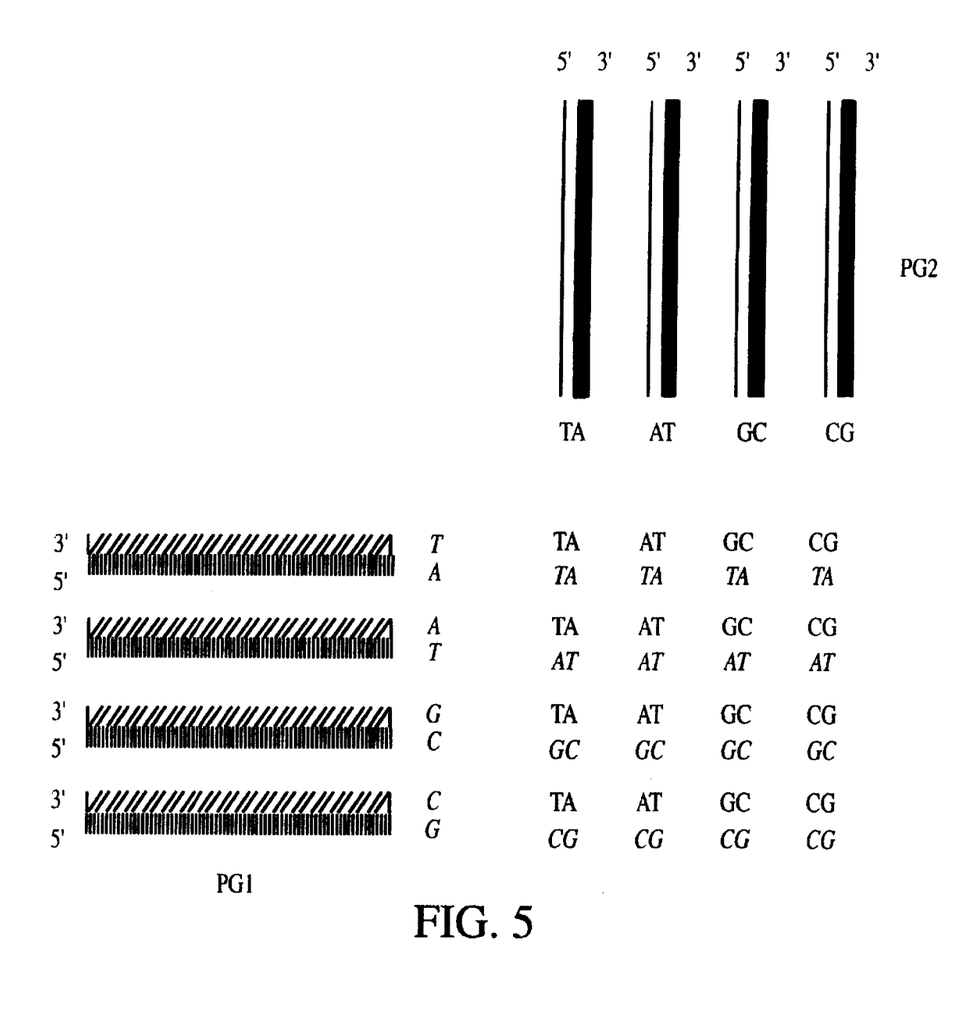
FIG. 5 shows an overview of the combination possibilities with 2×4 primer variants in the LCR.
Figure 6:
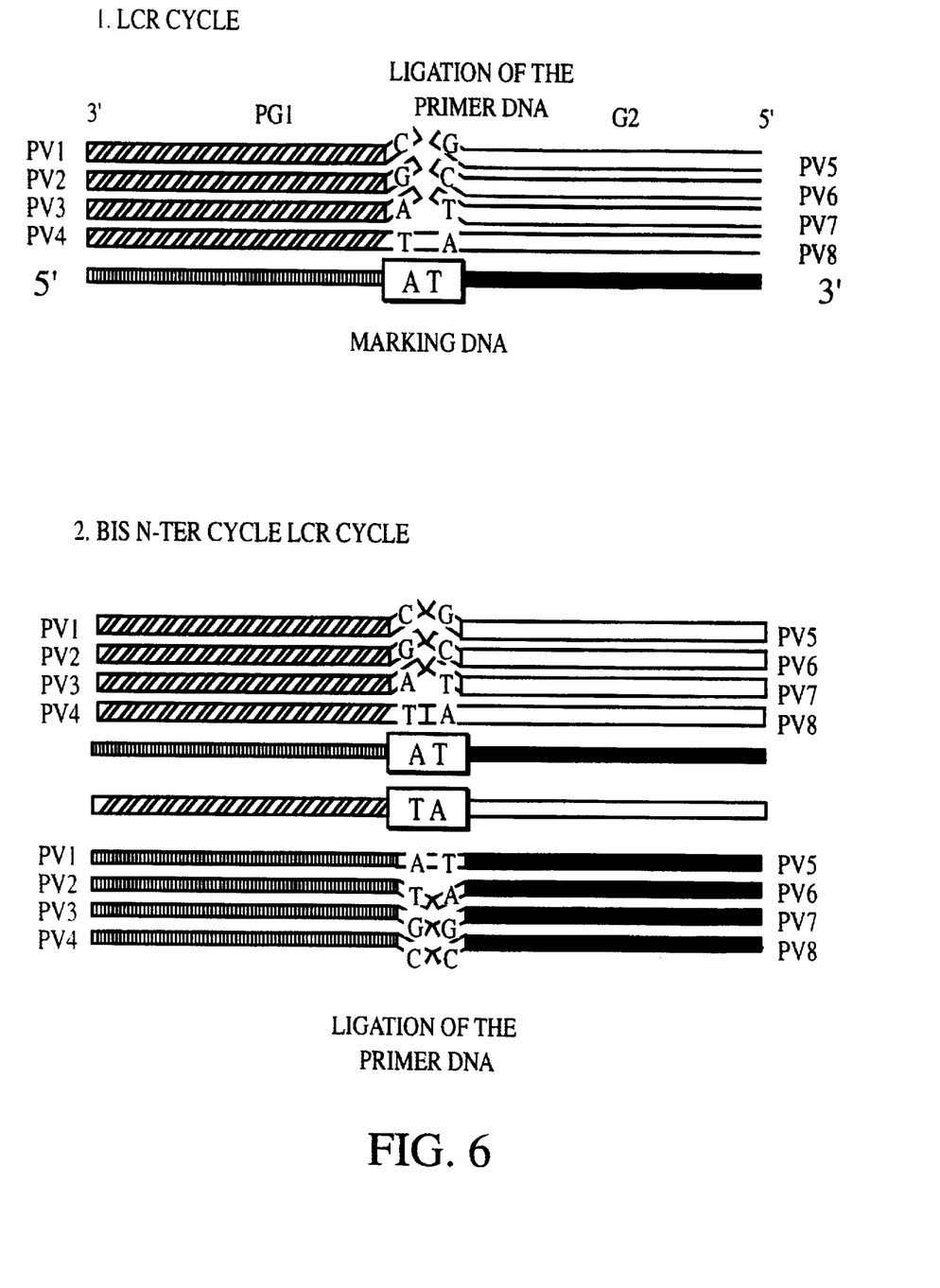
FIG. 6 shows a schematic representation of the functional mechanism of the duplication of the nucleic acid sequences by means of LCR.

FIGS. 5 and 6 show the combinations and the functional mechanism in the use of LCR. Double-stranded nucleic acid sequences, namely DNA sequences, are used here. For identification, double-stranded primer variants PV1–PV8 are used, which in turn are selected from a first PG1 and a second primer group PG2.

In the first cycle of the identification reaction shown in FIG. 6, the complementary counter-strand of the single-stranded nucleic acid sequence N is formed by ligation of the complementary primer variants PV4 and PV8. The nucleic acid sequence is amplified in the further cycles. As only one of the sixteen possible combinations of the primer variants PV1–PV8 is present in the identification reaction in each LCR batch, amplification only occurs in one of the sixteen reaction batches.

Figure 7:
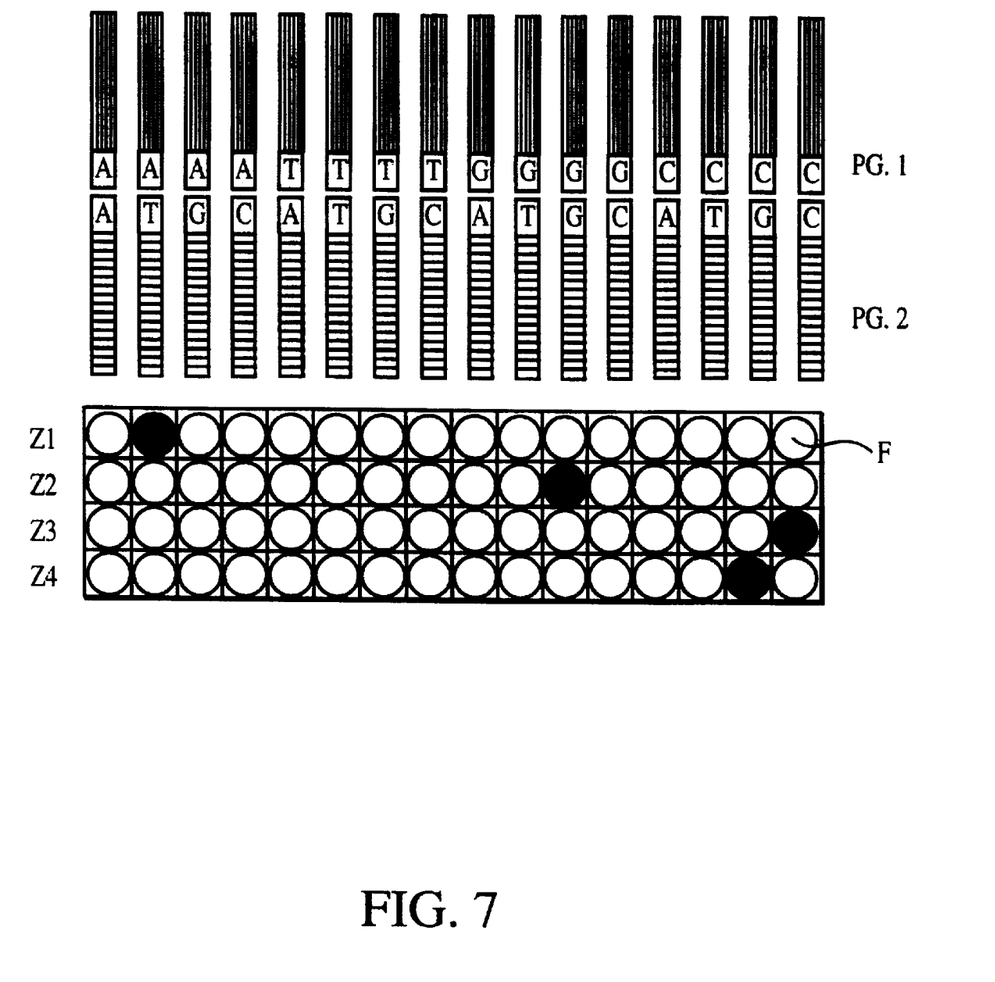
FIG. 7 shows the identification of a code and FIG. 8 shows a schematic representation of the functional mechanism for the minimization of base mispairings.
Figure 8:
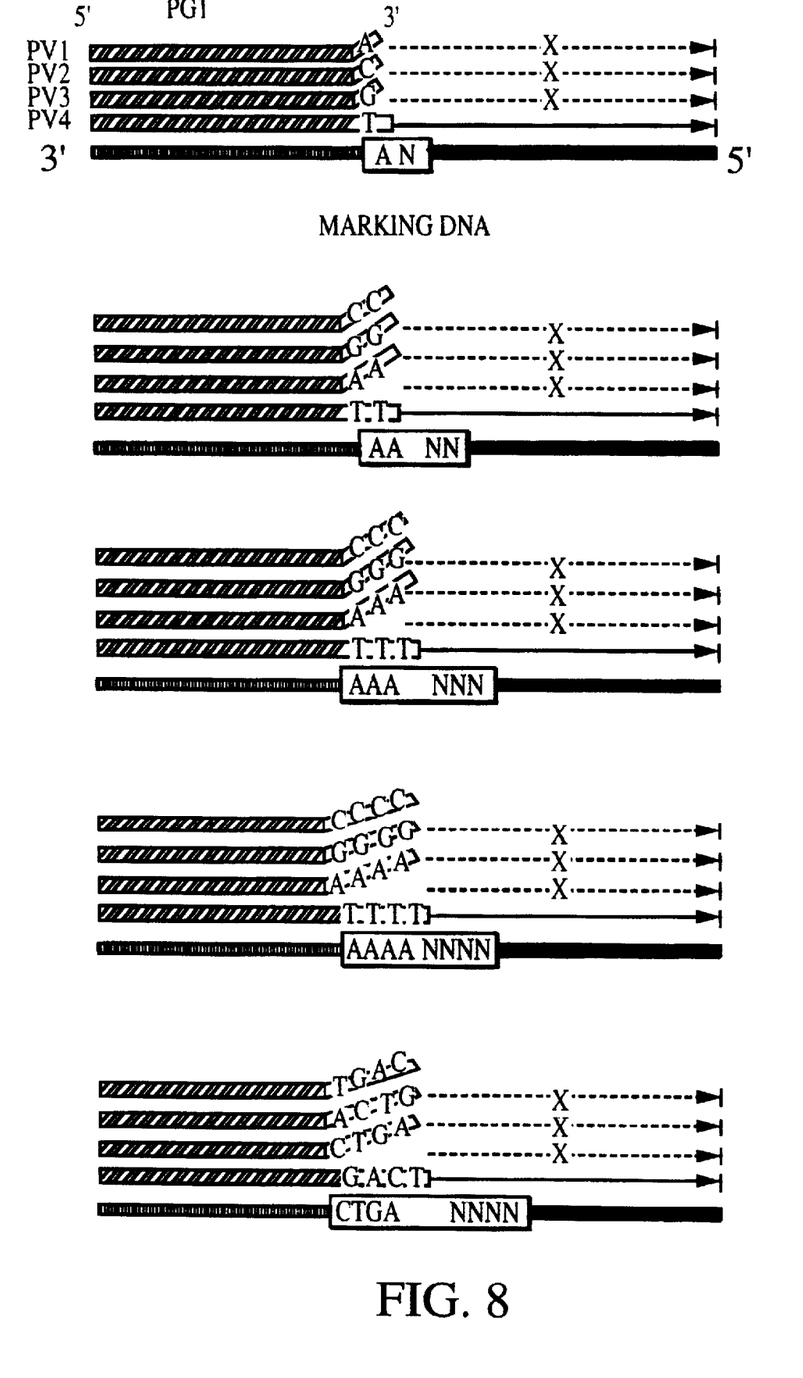

By way of example, FIG. 7 shows the identification of a complex code. The substance used for marking here contains four different nucleic acid sequences. Each of the nucleic acid sequences is selected from another nucleic acid set. Each nucleic acid set differs from the other nucleic acid sets in the first and third sequence section 1 and 3. The sixteen nucleic acid variants of each nucleic acid set in turn differ in the occupation of the two bases of the second sequence section 2.

For identification of the marking, a solution containing the four nucleic acid sequences is added to a microtiter plate which has four rows R1–R4 each having sixteen fields F. For amplification, the sixteen samples of the first row R1 are treated with two primer variants each, of which one are [sic] selected from a first PG1 and the other from a second primer group PG2. The first primer group PG1 has a sequence section which corresponds to the first sequence section 1 of a first nucleic acid sequence located in the sample. The second primer group PG2 has a sequence section which corresponds to the third sequence section 3 of the first nucleic acid sequence located in the sample. The two primer variants of the first and second primer group only hybridize with the first and third sequence section of the first nucleic acid set when agreement exists with the respective base of the second sequence section 2.

In each case two primer variants of a third and fourth, fifth and sixth and also seventh and eighth primer group are analogously added to the samples of the second, third and fourth rows R2 to R4. The previously mentioned primer groups in turn correspond to the first and/or third sequence section of the second, third and fourth nucleic acid set.

The code is defined such that the respective nucleic acid set determines the position in the code. Each nucleic acid variant is assigned a numerical value which determines the valency of the position. In the present example, the first position in the code is assigned the numerical value two, the second position the numerical value eleven, the third position the numerical value sixteen and the fourth position the numerical value fifteen.

FIGS. 8B–8E show nucleic acid sequences N, in which a number of bases are provided in each part region of the second section 2. As in FIGS. 8B–8D, a number of identical bases can be concerned here. As can be seen from FIG. 8E, however, combinations are also possible. The two part regions of the second sequence section 2 advantageously have the same length.

When using only one base in a part region, a mismatch and thus primer elongation can occur. In order to prevent such a faulty reaction, the respective part region can be occupied by a majority of bases.

The number of codes which can be produced using the process increases exponentially with the number of nucleic acid groups used. The number of nucleic acid sequences necessary for this, however, increases only linearly. As can be seen from the following table, a large number of codes can be produced using a comparatively small number of different nucleic acid sequences.

| Number of nucleic acid sets | Number of nucleic acid variants | Number of codes which can be produced |
| --- | --- | --- |
| 1 | 16 = 1 × 16 | $16^1$ = 16 |
| 2 | 32 = 2 × 16 | $16^2$ = 256 |
| 3 | 48 = 3 × 16 | $16^3$ = 4096 |
| 4 | 64 = 4 × 16 | $16^4$ = 65,536 |
| 5 | 80 = 5 × 16 | $16^5$ = 1,048,576 |
| 6 | 96 = 6 × 16 | $16^6$ = 16,777,216 |
| 7 | 112 = 7 × 16 | $16^7$ = 268,435,456 |
| 8 | 128 = 8 × 16 | $16^8$ = 4,294,967,296 |

A particularly preferred embodiment consists in forming the marking from five specified nucleic acid sets. 1,048,576 different markings can thus be provided. For identification, a 96-well microtiter plate is used in which a different mixture prepared from two primer variants is introduced into each well. The primer variants are in each case provided with a fluorophoric group such that a fluorescence signal is detectable on amplification. From the respective position of the fluorescence signals, it is possible to draw conclusions as to the combination of the primer variants and thus to the nucleic acid sequence contained in the marking. Such a process can be automated without great expenditure. It is inexpensive and quick to carry out.

The proposed biological marking can also be translated into a bar code. In this case, the number of specified nucleic acid units defines the number of bars of the bar code. The position of the bar in the bar code is fixed by the type of nucleic acid set and its width is fixed by the nucleic acid variant.

What is claimed is:

1. A process for marking solid, liquid or gaseous articles or substances, the process comprising:

providing the article or substance to be marked with at least one synthetically-prepared nucleic acid sequence, wherein said nucleic acid sequence has a first sequence section forming the 5'-terminal end, wherein said nucleic acid sequence has a second sequence section consisting of at least two bases connected to the first sequence section, and wherein said nucleic acid sequence has a third sequence section forming the 3'-terminal end connected to the second sequence section, wherein for identification of the nucleic acid sequence, there is provided a first primer group having a first primer section corresponding to the first sequence section and a second primer group having a third primer section corresponding to the third sequence section, wherein the first primer group and the second primer group each comprise four primer variants, wherein each primer variant differs in at least one additional terminally-provided base, wherein just one primer variant of the first primer group in combination with just one primer variant of the second primer group amplifies the nucleic acid sequence.

2. The process of claim 1, wherein the nucleic acid sequence has more than 20 nucleotides.

3. The process of claim 1, wherein the nucleic acid sequence has more than 40 nucleotides.

4. The process of claim 1, wherein a plurality of nucleic acid sequences are provided, wherein the plurality of nucleic acid sequences differ in the second sequence section.

5. The process of claim 1, wherein the second sequence section consists of two part regions, wherein at least one of the two part regions comprises a plurality of bases.

6. The process of claim 1, wherein the nucleic acid sequence of the first sequence section and the third sequence section differ from one another.

7. The process of claim 1, wherein the first sequence section and the third sequence section have the same number of nucleotides.

8. The process of claim 1, wherein the first sequence section hybridizes to the first primer section, wherein the third sequence section hybridizes to the third primer section, wherein the hybridizations occur under comparable stringency conditions.

9. The process of claim 1, wherein the primer variants hybridize to the nucleic acid sequence under comparable stringency conditions.

10. The process of claim 1, wherein the nucleic acid sequence comprises protein-like nucleic acid (PNA), phosphothionate nucleic acids (PTO) or hybrids thereof.

11. The process of claim 1, wherein each article or substance to be marked is provided with at least one distinguishable nucleic acid sequence.

12. The process of claim 1, wherein the nucleic acid sequence marking the solid articles or substances is covered by a protective layer.

13. The process of claim 12, wherein the nucleic acid sequence is a constituent of the protective layer.

14. The process of claim 1, wherein the article or substance to be marked is impregnated with the nucleic acid sequence.

15. The process of claim 1, wherein the nucleic acid sequence is admixed to the article or substance to be marked.

16. The process of claim 1, wherein the nucleic acid sequence is extracted or removed from the article or substance.

17. The process of claim 16, wherein a solution containing the extracted or removed nucleic acid sequence is prepared.

18. The process of claim 17, wherein the nucleic acid sequence contained in the solution is amplified by a polymerase chain reaction (PCR) using the primer variants.

19. The process of claim 18, wherein the amplified nucleic acid sequence is detected by fluorescence.

20. The process of claim 17, wherein the nucleic acid sequence contained in the solution is amplified by a ligase chain reaction (LCR) using the primer variants.

21. The process of claim 20, wherein the amplified nucleic acid sequence is detected by fluorescence.

22. A kit for identifying a marking on an article or substance, wherein the article or substance has been marked according to the process of claim 1, the kit comprising:

a first primer group having a first primer section corresponding to a first sequence section of a nucleic acid sequence; and a second primer group having a third primer section corresponding to a third sequence section of the nucleic acid sequence, wherein each primer group comprises four primer variants, wherein each primer variant differs in at least one additional terminally-provided base, wherein just one primer variant of the first primer group and just one primer variant of the second primer group are complementary to the nucleic acid sequence.

23. The kit of claim 22, wherein the primer variants have the same number of nucleotides.

24. The kit of claim 22, wherein each primer variant is more than 10 nucleotides in length.

25. The kit of claim 22, wherein each primer variant is more than 20 nucleotides in length.

26. The kit of claim 22, further comprising at least one nucleic acid sequence, wherein the nucleic acid sequence is one of a set of nucleic acid sequences, wherein each nucleic acid sequence within the set of nucleic acid sequences differs in the second sequence section.

27. The kit of claim 22, wherein each primer variant is associated with a carrier.

28. The kit of claim 27, wherein the carrier is a solution, a microtiter plate, a plastic or microcapsules.

29. The kit of claim 22, wherein a primer variant from the first primer group and a primer variant from the second primer group are associated with a carrier.

30. The kit of claim 22, wherein each primer variant comprises a fluorophoric group, wherein the fluorophoric group produces a fluorescence signal, wherein the fluorescence signal is used to detect amplification of the nucleic acid sequence.

31. A method of identifying a nucleic acid sequence marker on a solid, liquid or gaseous article or substance, the method comprising:

contacting the nucleic acid sequence marker with a primer variant from a first primer group and a primer variant from a second primer group under conditions such that amplification occurs if the primer variant from the first primer group and the primer variant from the second primer group hybridize to the nucleic acid sequence and amplification does not occur if the primer variant from the first primer group and the primer variant from the second primer group do not hybridize to the nucleic acid sequence, wherein the nucleic acid sequence marker on an article or substance can be identified based on the primer variant from the first primer group and the primer variant from the second primer group that amplifies the nucleic acid sequence.

32. A solid, liquid or gaseous article or substance marked with a nucleic acid sequence marker, wherein the article or substance has been marked by:

providing the article or substance to be marked with at least one synthetically-prepared nucleic acid sequence, wherein said nucleic acid sequence has a first sequence section forming the 5'-terminal end, wherein said nucleic acid sequence has a second sequence section consisting of at least two bases connected to the first sequence section, and wherein said nucleic acid sequence has a third sequence section forming the 3'-terminal end connected to the second sequence section, wherein for identification of the nucleic acid sequence, there is provided a first primer group having a first primer section corresponding to the first sequence section and a second primer group having a third primer section corresponding to the third sequence section, wherein the first primer group and the second primer group each comprise four primer variants, wherein each primer variant differs in at least one additional terminally-provided base, wherein just one primer variant of the first primer group in combination with just one primer variant of the second primer group amplifies the nucleic acid sequence.

* * * * *

UNITED STATES PATENT AND TRADEMARK OFFICE
CERTIFICATE OF CORRECTION

PATENT NO.    : 6,261,809 B1
DATED         : July 17, 2001
INVENTOR(S)   : Hans Kosak and Wolf Bertling It is certified that error appears in the above-identified patent and that said Letters Patent is hereby corrected as shown below:

Title page,
Item [56], References Cited, U.S. PATENT DOCUMENTS, please insert the following:

-- 5,139,812      08/1992        Lebacq
   5,643,728      07/1997        Slater et al. --.

FOREIGN PATENT DOCUMENTS, please insert the following:

-- WO 87/06383    10/1987        (WO)
   WO 89/07272    08/1989        (WO)
   WO 90/14441    11/1990        (WO)
   WO 91/17265    11/1991        (WO)
   WO 94/04918    03/1994        (WO)
   WO 95/02702    01/1995        (WO)
   WO 96/17954    06/1996        (WO)
   WO 96/19586    06/1996        (WO)
   WO 97/32040    09/1997        (WO)
   WO 98/55657    12/1998        (WO)
   44 39 896      05/1996        (DE) --.

OTHER PUBLICATIONS, please insert the following:

-- Sano et al., "Deoxyribonucleic acids as unique markers in molecular detection, Genetic Analysis: Biomolecular Engineering, 14(2):37-40 (1997) --.

UNITED STATES PATENT AND TRADEMARK OFFICE
CERTIFICATE OF CORRECTION

PATENT NO. : 6,261,809 B1
DATED : July 17, 2001
INVENTOR(S) : Hans Kosak and Wolf Bertling It is certified that error appears in the above-identified patent and that said Letters Patent is hereby corrected as shown below:

Column 1,
Line 61, please delete "1 and 20" and insert -- 1, 22, 31, and 32 -- therefor.
Line 62, please delete "19 and 21" and insert -- 21 and 23 -- therefor.
Line 63, please delete "27" and insert -- 30 -- therefor.

Column 4,
Line 8, after "seen" and before "FIG. 2" please insert -- from --.

Signed and Sealed this

Ninth Day of April, 2002

Attest:

JAMES E. ROGAN
*Attesting Officer*  *Director of the United States Patent and Trademark Office*